United States Patent
Stoppler

(10) Patent No.: US 6,676,687 B2
(45) Date of Patent: Jan. 13, 2004

(54) FOOT TANNING APPARATUS

(76) Inventor: Deborah Gina-Marie Stoppler, 9280 E. Thompson Peak Pkwy. #36, Scottsdale, AZ (US) 85255

( * ) Notice: Subject to any disclaimer, the term of this patent is extended or adjusted under 35 U.S.C. 154(b) by 0 days.

(21) Appl. No.: 10/006,840

(22) Filed: Nov. 5, 2001

(65) Prior Publication Data

US 2003/0088297 A1 May 8, 2003

(51) Int. Cl.[7] ................................................ A61N 5/06
(52) U.S. Cl. ........................................ 607/94; 607/90
(58) Field of Search ...................................... 607/88–94

(56) References Cited

U.S. PATENT DOCUMENTS

| | | |
|---|---|---|
| 508,231 A | 11/1893 | Meeker |
| 558,394 A | 4/1896 | Kellogg |
| 670,184 A | 3/1901 | Morrison |
| 720,357 A | 2/1903 | Joachimson |
| 853,033 A | 5/1907 | Roberts |
| 2,054,332 A | 9/1936 | Lower et al. |
| 2,311,415 A | 2/1943 | Rouat |
| 3,981,030 A | 9/1976 | Turner |
| 4,140,128 A | 2/1979 | Van Der Schaaf |
| 4,444,189 A | 4/1984 | Seiverd |
| 4,582,062 A | 4/1986 | Albini |
| 4,674,507 A | 6/1987 | Basso |
| 4,964,183 A | 10/1990 | LaForce, Jr. |
| 4,984,571 A * | 1/1991 | Springer et al. ............... 607/94 |
| 5,466,248 A | 11/1995 | Whitson-Newman |
| 5,557,112 A * | 9/1996 | Csoknyai et al. ....... 250/504 R |
| 5,565,685 A * | 10/1996 | Czako et al. ........... 250/504 R |
| 5,733,314 A | 3/1998 | Perrino |
| 5,830,123 A | 11/1998 | Franz et al. |
| 6,273,906 B1 * | 8/2001 | Swanson ..................... 607/91 |

* cited by examiner

Primary Examiner—Roy D. Gibson
Assistant Examiner—Henry M. Johnson, III
(74) Attorney, Agent, or Firm—Michael I. Kroll

(57) ABSTRACT

The present invention 10 discloses a tanning device for the ankle and foot 14 area of a user 12 comprising a housing 16 having upper positioned apertures 30 for inserting the feet 14. The apertures 30 have elastic-like sleeves 18 therein which sleeves have apertures 40 therein that form a seal around the inserted appendage. The elastic-like sleeves 18 are constructed from suitable material having UV light-blocking properties so that only the appendage 14 within the housing 16 receives the UV rays. Lining the inner surfaces of the housing 16 are a plurality of ultraviolet bulbs 38 activated by an on/off toggle switch 26. Positioned within the rear wall of the device are a plurality of fans 32 moving exterior ambient air into the device that exits through either the screen floor 36 substantially forming the base of the device or a plurality of apertures forming vents 20 within the exterior walls. Also positioned on the exterior side wall of the device are the power switch 26 and a control knob 28 for setting a run time for the fans 32.

13 Claims, 10 Drawing Sheets

FOOT TANNING APPARATUS

BACKGROUND OF THE INVENTION

1. Field of the Invention

The present invention relates generally to tanning devices and more specifically to a tanning device for ankle and foot area. The present invention is comprised of a housing having upper positioned apertures for inserting feet. The apertures have elastic-like sleeves that form a seal around the inserted appendage. The elastic-like sleeves are constructed from suitable material having UV light-blocking properties. Therefore, only the appendage within the housing receives the UV rays.

Lining the inner surfaces of the housing are a plurality of ultraviolet bulbs activated by a toggle switch that produce an environment inside the housing ideal for tanning consisting of an abundance of ultraviolet A light waves; ultraviolet B light waves.

Positioned within the rear wall of the device is a plurality of fans moving exterior ambient air into the device that exits through either the screen floor substantially forming the base of the device or a plurality of apertures forming vents within the exterior walls. Also positioned on the exterior side wall of the device are a power switch and a control knob for energizing the fans and setting a run time for the fans.

2. Description of the Prior Art

There are other tanning devices designed for tanning human beings. Typical of these is U.S. Pat. No. 508,231 issued to Meeker on Nov. 7, 1893.

Another patent was issued to Kellog on Apr. 14, 1896 as U.S. Pat. No. 558,394. Yet another U.S. Pat. No. 670,184 was issued to Morrison on Mar. 19, 1901 and still yet another was issued on Feb. 10, 1903 to Joachimson as U.S. Pat. No. 720,357.

Another patent was issued to Roberts on May 7, 1907 as U.S. Pat. No. 853,033. Yet another U.S. Pat. No. 2,054,332 was issued to Lower on Sep. 15, 1936. Another was issued to Turner on Sep. 21, 1976 as U.S. Pat. No. 3,981,030 and still yet another was issued on Feb. 20, 1979 to Van Der Schaaf as U.S. Pat. No. 4,140,128.

Another patent was issued to Seiverd on Apr. 24, 1984 as U.S. Pat. No. 4,444,189. Yet another U.S. Pat. No. 4,582,062 was issued to Albini on Apr. 15, 1986. Another was issued to Laforce on Oct. 23, 1990 as U.S. Pat. No. 4,964,183 and still yet another was issued on Nov. 14, 1995 to Newman as U.S. Pat. No. 5,466,248.

Another patent was issued to Perrino on Mar. 31, 1998 as U.S. Pat. No. 5,733,314. Yet another U.S. Pat. No. 5,830,123 was issued to Franz on Nov. 3, 1998.

U.S. Pat. No. 508,231

Inventor: G. Meeker

Issued: Nov. 7, 1893

In an apparatus for curing diseases, the combination, with a reflector and a light arranged therein, of a frame provided with an adjustably arranged glass pane, a screen forming a chamber in front of said pane, and a blanket support removably and adjustably arranged on said screen, consistently essentially of a collar, arms, and holding claws, substantially as and for the purposes set forth.

U.S. Pat. No. 558,394

Inventor: J. H. Kellogg

Issued: Apr. 14, 1896

An apparatus for applying radiant heat for bath purposes, comprising a chamber whose walls are provided with mirrors on its vertical opposite sides and horizontal top, the mirrors being arranged to reflect light toward the center of the chamber, and lamps arranged within the chamber on the walls thereof and inclosing between them a free central space for the reception of the person, or that part of his body which is to be treated, substantially as described.

U.S. Pat. No. 670,184

Inventor: W. B. Morrison

Issued: Mar. 19, 1901

In a radiant-heat bath, a cabinet provided with an opening, an arc lamp with its arc-forming part extending through said opening into the interior of said cabinet, a reflector surrounding the light-producing part of said lamp consisting of two movable members adapted to be moved together to concentrate the light or moved apart to diffuse the same, mechanism operated from the exterior of the cabinet for adjusting said members to regulate the light.

U.S. Pat. No. 720,357

Inventor: M. Joachimson

Issued: Feb. 10, 1903

In a radiant-heat bath, the combination, with two light sources, of a double faced mirror arranged between them and adapted to be swung over either one for cutting off the light from the same, substantially as set forth.

U.S. Pat. No. 853,033

Inventor: H. H. Roberts

Issued: May 7, 1907

A portable electric bath cabinet, consisting of a casing open upon one side and closed upon the other sides, groups of different colored electric lamps projecting into the box in a mixed relation, a duplex cable having one of its wires connected to one terminal of each lamp, a compound switch having one of its members connected to the other wire of the duplex cable, said switch having a plurality of opposite contacts each connected respectively to the other terminal of a lamp and each of said contacts being exclusively connected to lamps of the same color.

U.S. Pat. No. 2,054,332

Inventor: A. E. Lower

Issued: Sep. 15, 1936

A therapeutic lamp comprising a cabinet having an opening for the insertion of the member to be treated, means in the cabinet to support a foot in an upstanding position from the heel said means being above the bottom of the cabinet, heat generating means in the cabinet above said supporting means, side walls on the cabinet extending below said supporting means, and means hinging one such wall along its top edge adjacent the supporting means to the adjacent side of the cabinet for upward and inward raising movement, the height of said hinged wall being substantially the same as the width of the cabinet whereby when said wall is swung up it will form a bottom closure for the cabinet immediately below the supporting means.

U.S. Pat. No. 2,311,415

Inventor: R. Rouat

Issued: Mar. 2, 1939

In an electric bath, an electric element or elements and reflectors for projecting rays onto the body of the user and a cabinet having a bottom of sufficient length and width to permit the body of the user to lie thereon while in a reclining or prone position, said cabinet having openings in the top, flexible springy means closing said openings having slits therein permitting the hands and arms of the user to be thrust through said slits to the exterior of said cabinet, said slits closing together and closing said opening automatically upon the removal of the arms and hands.

U.S. Pat. No. 3,981,030

Inventor: Jeanette A. Turner

Issued: Sep. 21, 1976

A base having a pair of spaced apart, upstanding end members, which are so configured and spaced apart as to maintain the feet of the sunbather in an erect position thereby insuring proper orientation of the legs to provide an even tan.

U.S. Pat. No. 4,140,128

Inventor: Joe Van Der Schaaf

Issued: Feb. 20, 1979

A sun tanning table adapted to support the body of the user for sun tanning purposes, including a base adapted to be supported on the ground, and a substantially flat table top mounted on the base for supporting the body of the user in a reclining position for sun tanning purposes. A device is provided for mounting rotatably the table top on the base to enable the table top to rotate continuously through 360 degrees relative to the base. A motor rotates the table top about its vertical axis relative to the base to enable the user to attain a uniform sun tan.

U.S. Pat. No. 4,444,189

Inventor: Paul J. Seivard

Issued: Apr. 24, 1984

A phototherapy booth is provided with sources of fluorescent black light for use by persons suffering from a medical skin disorder. The booth includes at least three walls made from a rigid perforated substrate to facilitate dissipation of heat. At least one lamp on each wall is vertically adjustable along a track for increasing the eight of light exposure. The walls may be vertically disposed for use by a person who is ambulatory or may be arranged as a tunnel for use by a person who is bedridden.

U.S. Pat. No. 4,582,062

Inventor: Mark R. Albini

Issued: Apr. 15, 1986

The present invention relates to an apparatus for tanning which may be easily and conveniently used inside the home. The invention employs a tent structure which can be disassembled and stored in a small place and a conventional sunlamp. The interior surfaces of the tent structure are made of a reflective material. The sunlamp is positioned between the reflective surfaces. In use, a person lies in the interior of the structure below the sunlamp. The person receives direct ultraviolet rays from the sunlamp but in addition receives reflected multidirectional ultraviolet rays from the interior reflective surfaces. The reflected rays increase the surface of the skin which may be reached by ultraviolet rays thereby promoting a more even tan.

U.S. Pat. No. 4,674,507

Inventor: Marlene Basso

Issued: Jun. 23, 1987

A tanning booth is provided which creates an even tanning effect and includes either a combination of UVB and UVA lamp or a novel ultraviolet lamp emitting radiation in the specific 300–340 nm range. The booth is formed as a cylinder which is rotated at a constant speed so as to provide an even tan to a user who is stationary at the axis of the cylinder.

U.S. Pat. No. 4,964,183

Inventor: James W. LaForce

Issued: Oct. 23, 1990

The invention provides a tanning tub which can be inflated for use and deflated for transporting and for storage. Two tubular walls vertically stacked support a tubular air mattress attached suspended centrally between the walls. The tubes in the tubular mattress have clear plastic upper surfaces and the opposite tube sides are fabricated of silvery colored material. The tubular walls and the tubular mattress when inflated form into a water proof container which can be used by a sunbather to relax in a cool pool of water. The clear top and silvery bottom arrangement of the mattress tubes allows a sunbather to tan on both sides at the same time, one side by direct exposure and the other side by reflection. The inflated tanning tub can be used as a float in a pool, for tanning dry on land, and as a bed for camping or a spare bed at home.

U.S. Pat. No. 5,466,248

Inventor: Jayne C. Whitson-Newman

Issued: Nov. 14, 1995

A foot ghost ender comprised of a rounded steel shell having a front, a back, a left sidewall, a right sidewall, an open top, a closed bottom, an inner surface, and an outer surface. An aperture is formed in the right sidewall. An extension is integral with the open top. The extension has an open circular top. A plurality of tanning lamps is secured to the inner surface of the rounded steel shell. An adjustable foot rest is secured to the inner surface of the rounded steel shell. The device also contains a retractable power cord having a first end, and a second end. The first end is received through the aperture formed within the right sidewall of the rounded steel shell. A three-prong polarized plug secured to the first end. A control panel with adjustable timer is secured to the right sidewall of the rounded steel wall. The adjustable timer functions to turn the tanning lamps on and off.

U.S. Pat. No. 5,733,314

Inventor: Joseph M. Perrino

Issued: Mar. 31, 1998

A portable solar tanning spa having a longitudinally extending first half section and a longitudinally extending second half section, each being formed of a light transparent material. The first half section and the second half section are rotatably connected such that the second half section may rotate into a position parallel with the first half section to allow the user to enter and exit as desired. In a preferred embodiment of the present invention, the longitudinally extending first half section and the longitudinally extending second half section are arranged in a vertical position and are pivotally connected to the rim of a back member to allow the first half section and the second half section to swing outwardly into an open position and inwardly into a closed position. In another preferred embodiment of the present invention, the first half section and the second half section form a cylindrical enclosure having an opening for receiving a door to allow the user to enter or exit the spa as desired.

U.S. Pat. No. 5,830,123

Inventor: Wolfgang Franz

Issued: Nov. 3, 1998

A pivotable irradiating device for a person on a lying surface provides extensively uniform continued irradiation of the lying surface without any interruption in time when the irradiating device is pivoted out of the starting position. The irradiating device has at least one radiator in a housing. The housing is connected to a securing element via a rotatable connector (hinge). The axis of rotation of the hinge is located outside a central axis of the irradiating device. The intersection of these two axes is located in the center of the lying surface or in its vicinity.

While these tanning devices may be suitable for the purposes for which they were designed, they would not be as suitable for the purposes of the present invention, as hereinafter described.

SUMMARY OF THE PRESENT INVENTION

The present invention discloses a tanning device for the ankle and foot area of a user comprising a housing having upper positioned apertures for inserting the feet. The apertures have elastic-like sleeves having apertures therein that form a seal around the inserted appendage. The elastic-like sleeves are constructed from suitable material having UV light-blocking properties so that only the appendage within the housing receives the UV rays. Lining the inner surfaces of the housing are a plurality of ultraviolet bulbs activated by an on/off toggle switch. Positioned within the rear wall of the device are a plurality of fans moving exterior ambient air into the device that exits through either the screen floor substantially forming the base of the device or a plurality of apertures forming vents within the exterior walls. Also positioned on the exterior side wall of the device are the power switch and a control knob for setting a run time for the fans.

A primary object of the present invention is to provide a tanning device for a users feet.

Another object of the present invention is to provide a foot tanning device having apertures for inserting a user's feet for a tanning session.

Yet another object of the present invention is to provide elastic-like sleeves engaging the periphery of said apertures that have ultraviolet light blocking properties.

Still yet another object of the present invention is to provide elastic-like sleeves that forms a seal around an inserted appendage.

Another object of the present invention is to provide a foot tanning device with a ventilation system comprising fans, a screen base and vents to prevent accumulation of heat within the device.

Yet another object of the present invention is to provide a tanning device with a plurality of ultraviolet A and ultraviolet B emitting bulbs positioned within the interior of the device.

Still yet another object of the present invention is to provide a tanning device with a plurality of ultra violet bulbs positioned so as to generate ultraviolet rays encompassing all sides of the appendage.

Another object of the present invention is to provide a tanning device having an exterior switch control for energizing the ultraviolet bulbs and ventilation fans.

Additional objects of the present invention will appear as the description proceeds.

The present invention overcomes the shortcomings of the prior art by providing a tanning device that isolates the tanning procedure exclusively to the portion of the limb that is inserted into the device through the UV blocking elastic-like sleeve that seals around the inserted appendage.

Further, the interior of the device has a plurality of ultraviolet bulbs emitting in combination ultraviolet A and B light waves that encompasses all sides of the inserted appendage.

The present invention also provides an external switch to activate the interior lighting and ventilation system consisting of one or more fans positioned within the exterior wall drawing ambient air into the device that exits through a screen platform substantially forming the base of the device or through a plurality of apertures within the walls of the device forming vents.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
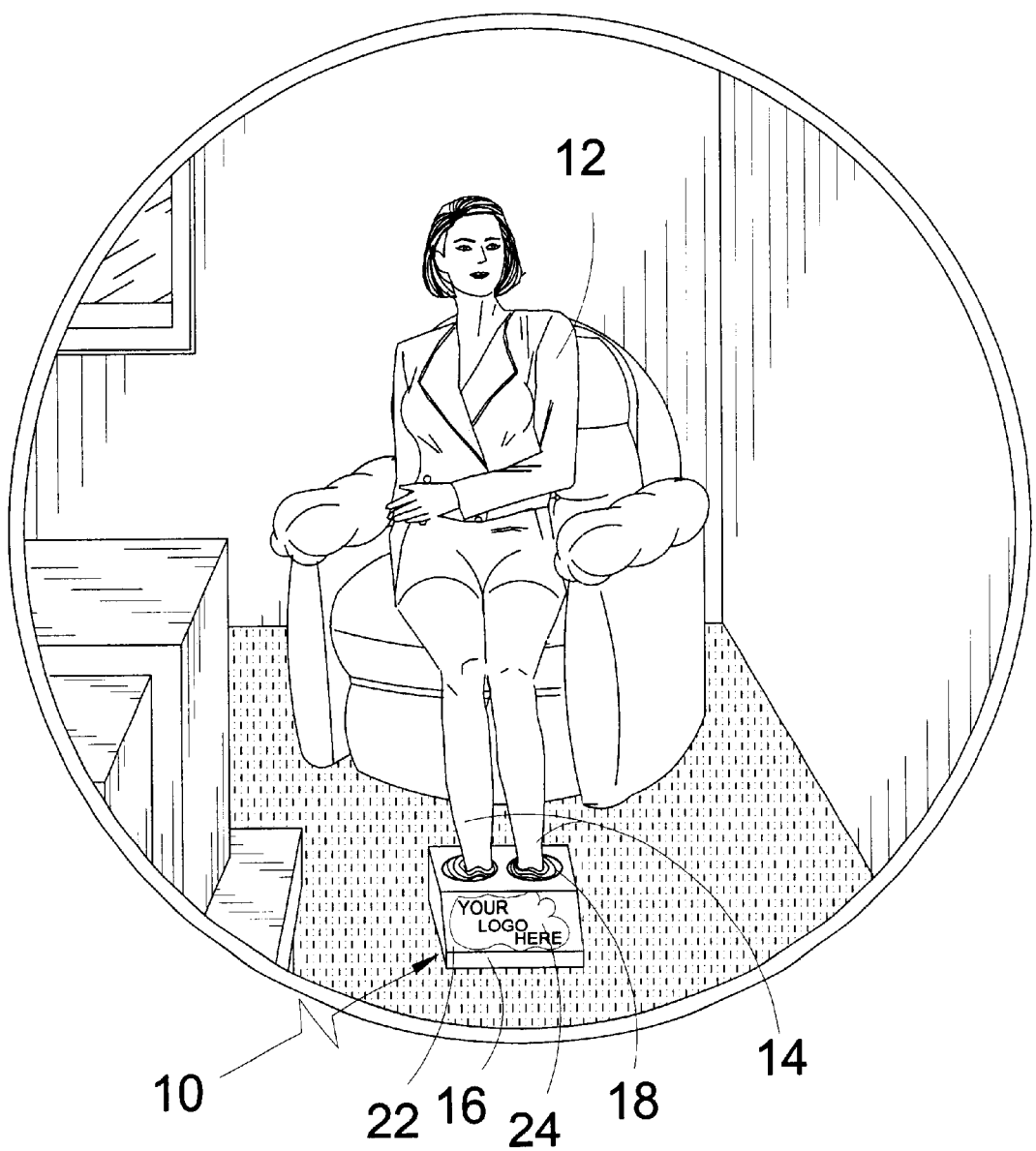
FIG. 1 is a perspective view of the present invention in use.

With regard to reference numerals used, the following numbering is used throughout the drawings.

10 present invention
12 user
14 feet
16 housing
18 leg sealing means
20 air vents
22 forward surface
24 logo
26 on/off switch
28 timer/fan switch
30 housing aperture
32 intake fans
34 power source
36 bottom screen
38 UV bulbs
40 seal aperture
42 direction arrows

DETAILED DESCRIPTION OF THE PREFERRED EMBODIMENT

The following discussion describes in detail one embodiment of the invention and several variations of that embodiment. This discussion should not be construed, however, as limiting the invention to those particular embodiments, practitioners skilled in the art will recognize numerous other embodiments as well. For definition of the complete scope of the invention, the reader is directed to appended claims.

Turning to FIG. 1, shown therein is a perspective view of the present invention 10 in use showing the user 12 having both feet 14 inserted into a housing 16 having leg sealing 18 for limiting exposure of ultraviolet rays to the skin surfaces of the limb enclosed. The housing 16 has a forward facing surface 22 upon which a logo 24 or the like could be placed.

Figure 2:
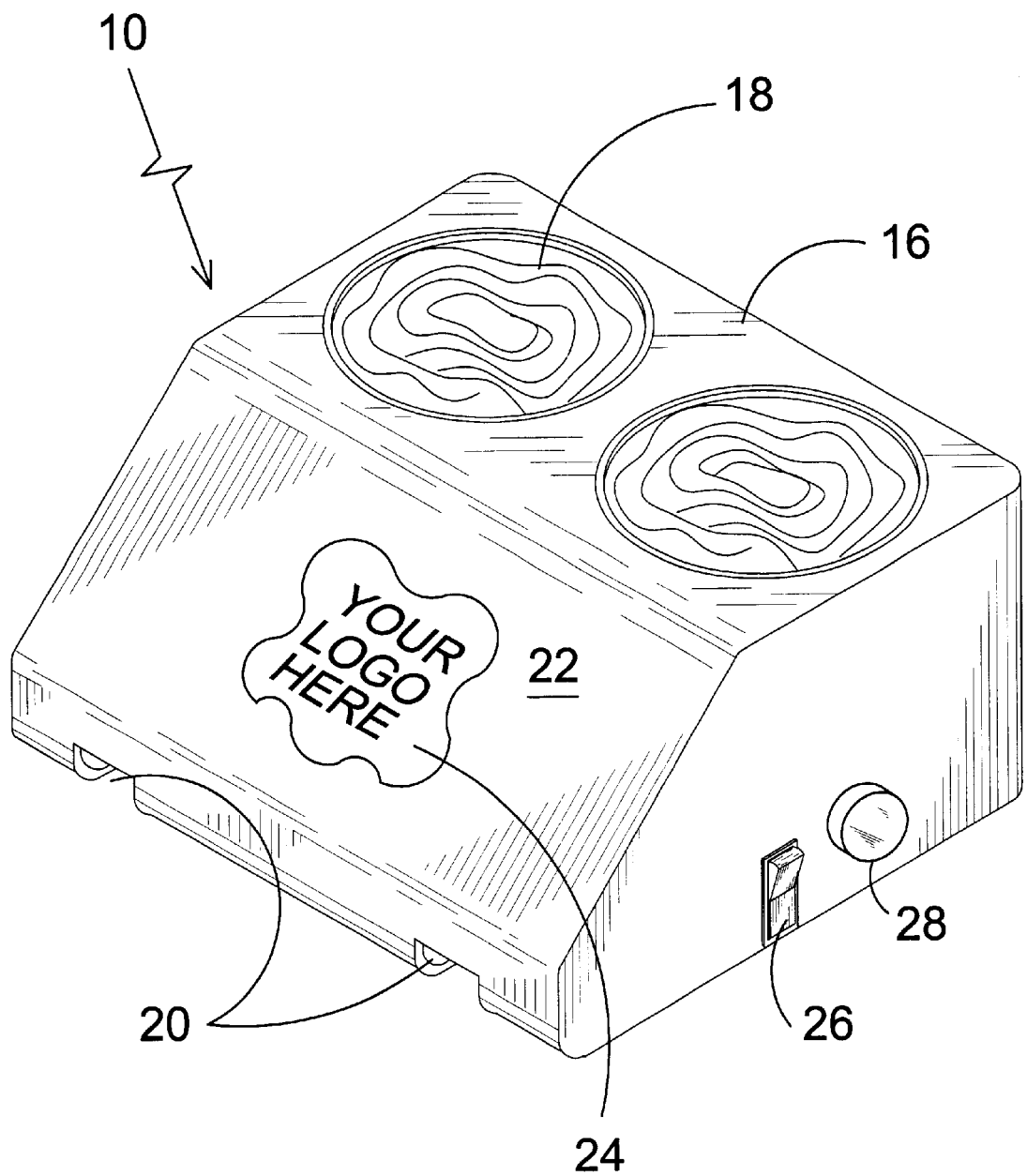
FIG. 2 is a perspective view of the present invention.

Turning to FIG. 2, shown therein is a perspective view of the present invention 10 showing the present invention having a plurality of air vents 20 to allow for ambient air circulation from the rearwardly positioned fans (not shown, see FIG. 3) across the users feet and out through the forwardly positioned vents 20. Also shown are an on/off switch 26, a timer/fan switch 28 and other elements previously disclosed.

Figure 3:
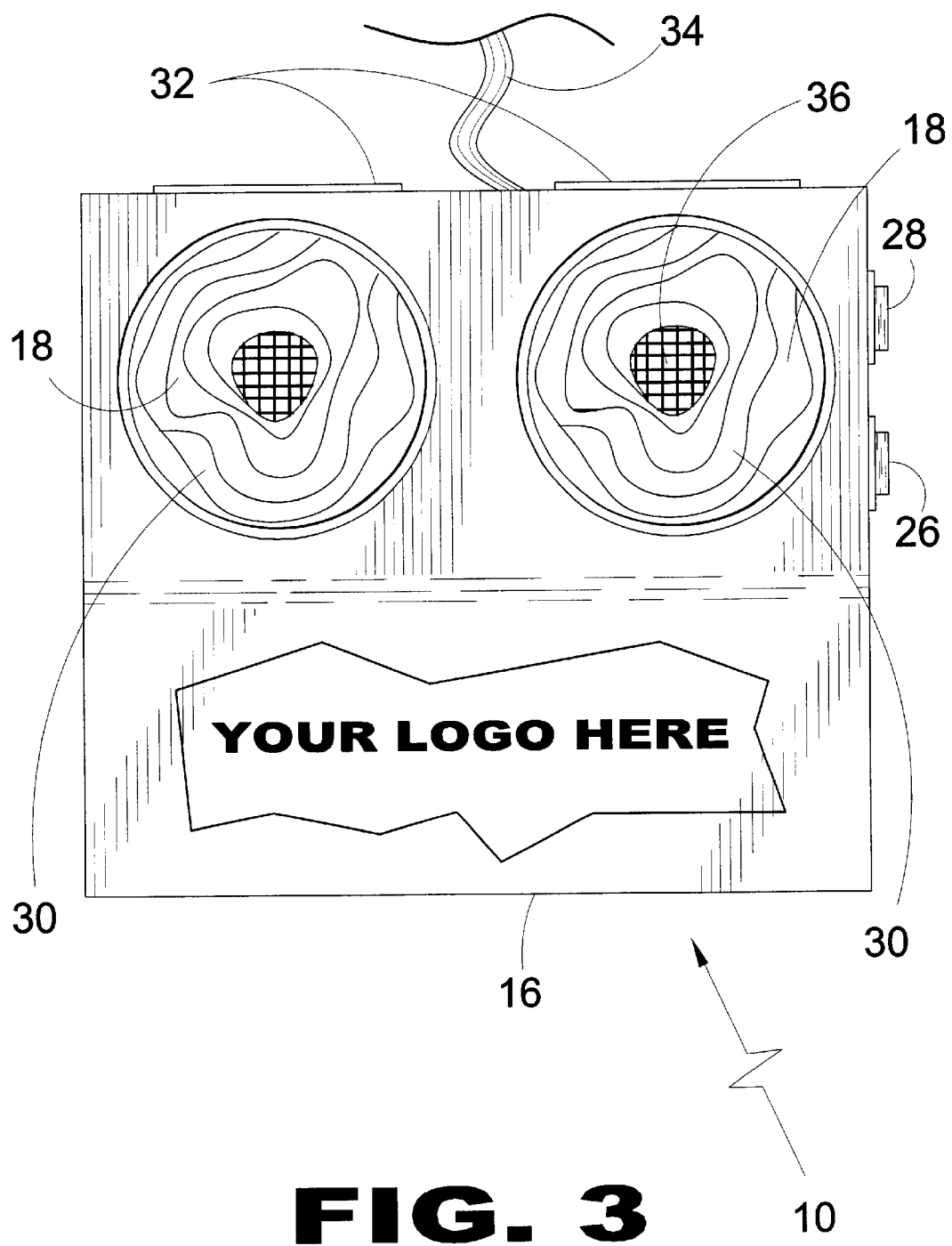
FIG. 3 is a top view of the present invention.

Turning to FIG. 3, shown therein is a top view of the present invention 10 showing the present invention having apertures 30 with sealing means 18 for the insertion of the limbs to be tanned. The apertures 30 have elastomeric members 18 that will seal around the user's limbs. Also shown are multiple air intake fans 32, a power source 34, a bottom screen 36 and other elements previously disclosed.

Figure 4:
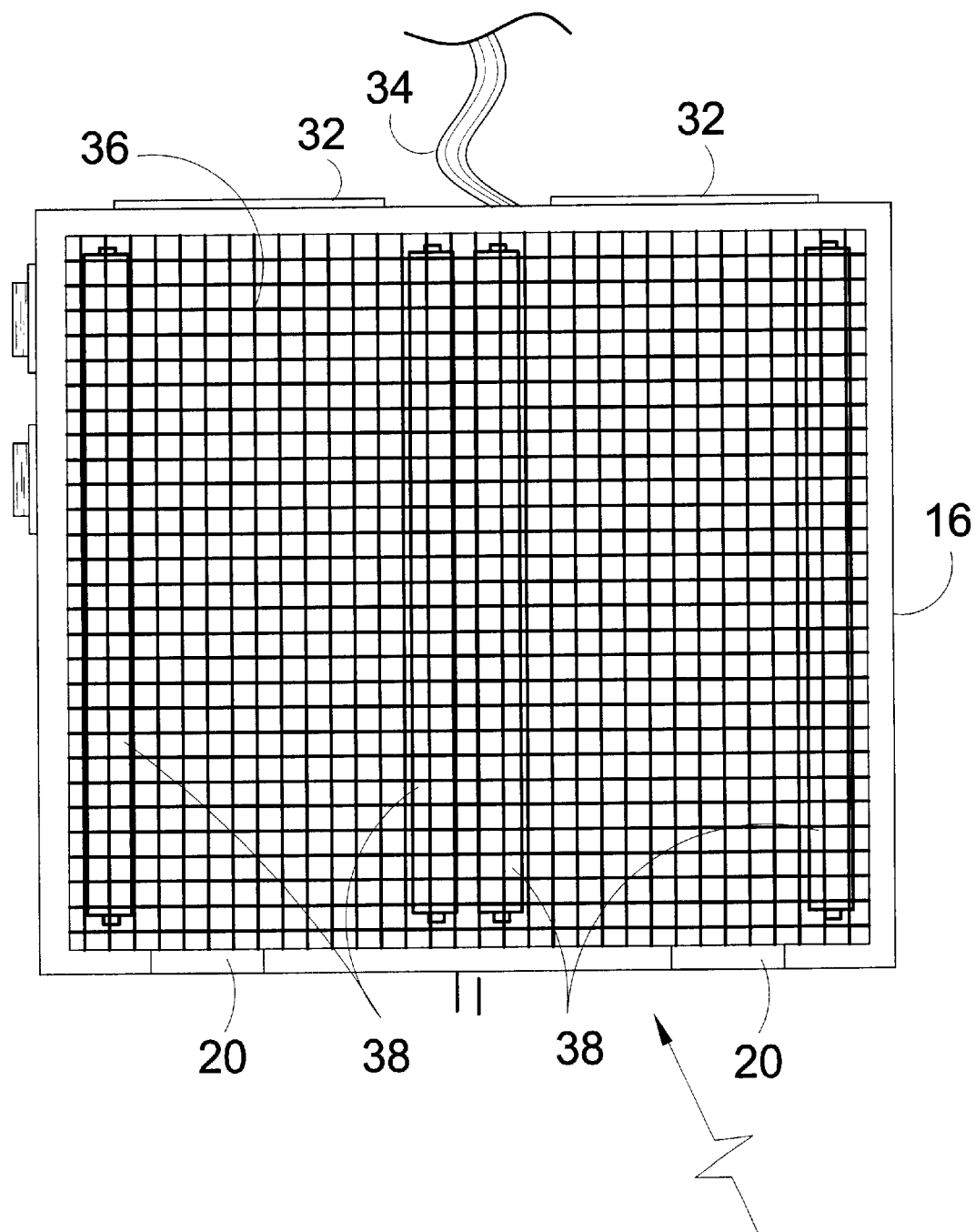
FIG. 4 is a bottom view of the present invention.

Turning to FIG. 4, shown therein is a bottom view of the present invention 10 showing a removable screen platform 36 for supporting the feet of the user. The screen also provides for air circulation around the feet of the user during a tanning session. Also shown are a plurality of ultraviolet A and ultraviolet B generating bulbs 38 positioned around the interior of the housing 16 of the device. Other elements previously disclosed are also shown.

Figure 5:
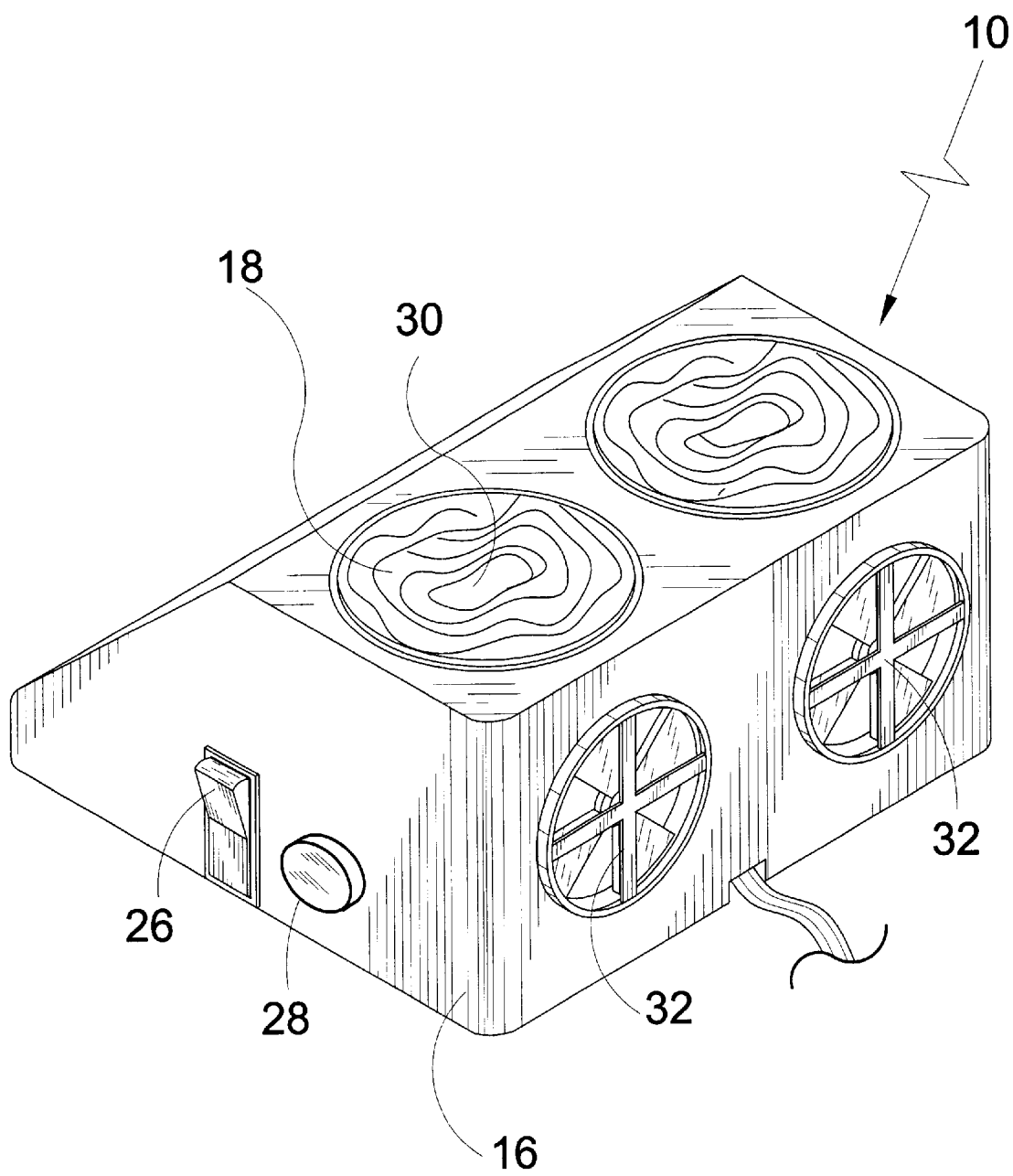
FIG. 5 is a perspective view of the present invention.

Turning to FIG. 5, shown therein is a perspective view of the present invention 10 showing the rear of the tanning device having at least one fan 32 for introducing ambient air into the tanning chamber. Also shown is a toggle switch 26 for energizing the ultraviolet lights and fans. Other elements previously disclosed are also shown.

Figure 6:
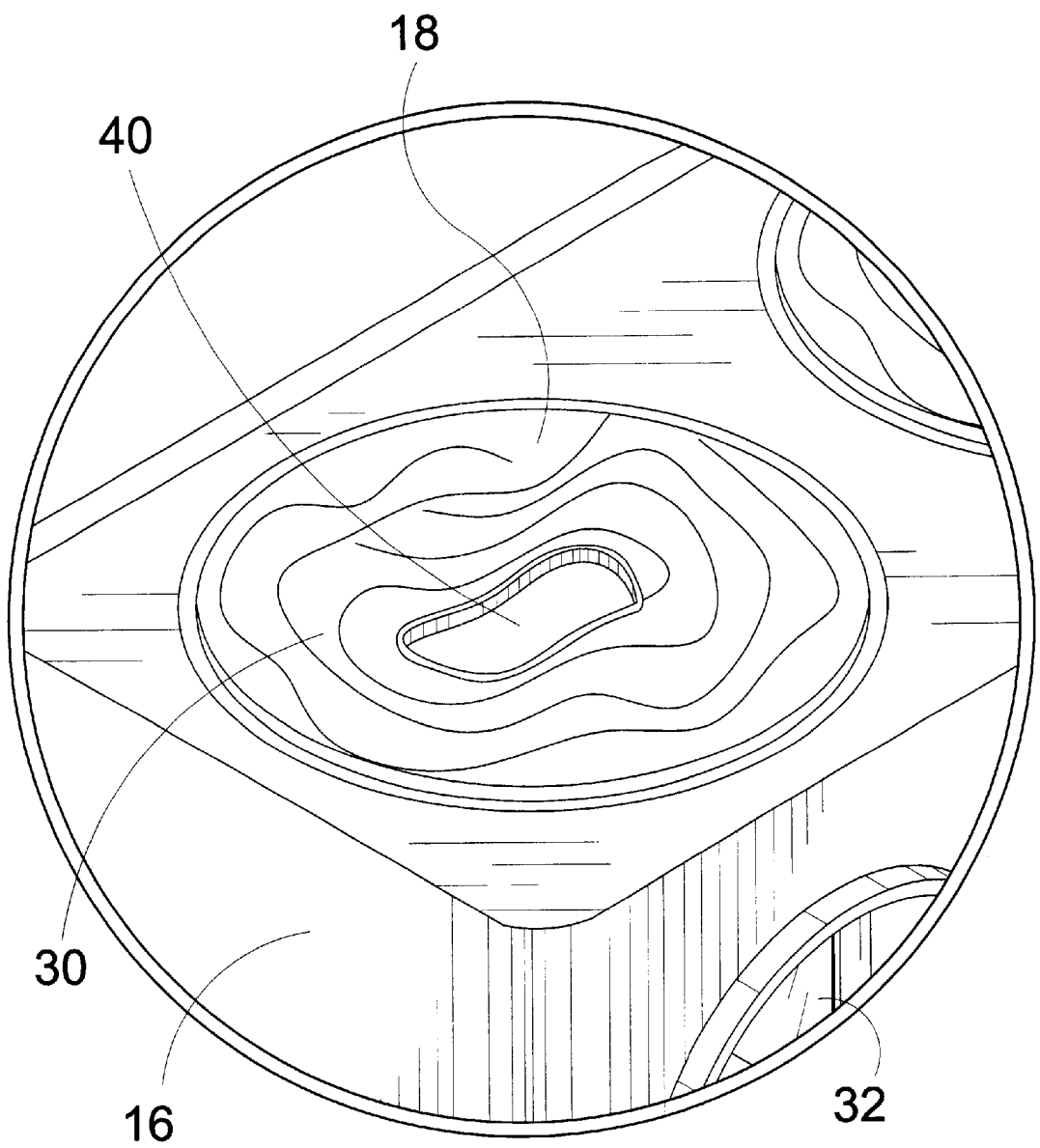
FIG. 6 is an enlarged view of the limb aperture.

Turning to FIG. 6, shown therein is an enlarged view of the limb aperture 40 of the leg sealing means 18 disposed in the housing aperture 30 comprising an elastomeric UV ray blocking material. The material 18 has a centrally positioned opening 40 wherethrough a limb can be inserted for tanning treatment. The elastomeric member 18 will close to a skin engaging position preventing release of ultraviolet rays. Other elements previously disclosed are also shown.

Figure 7:
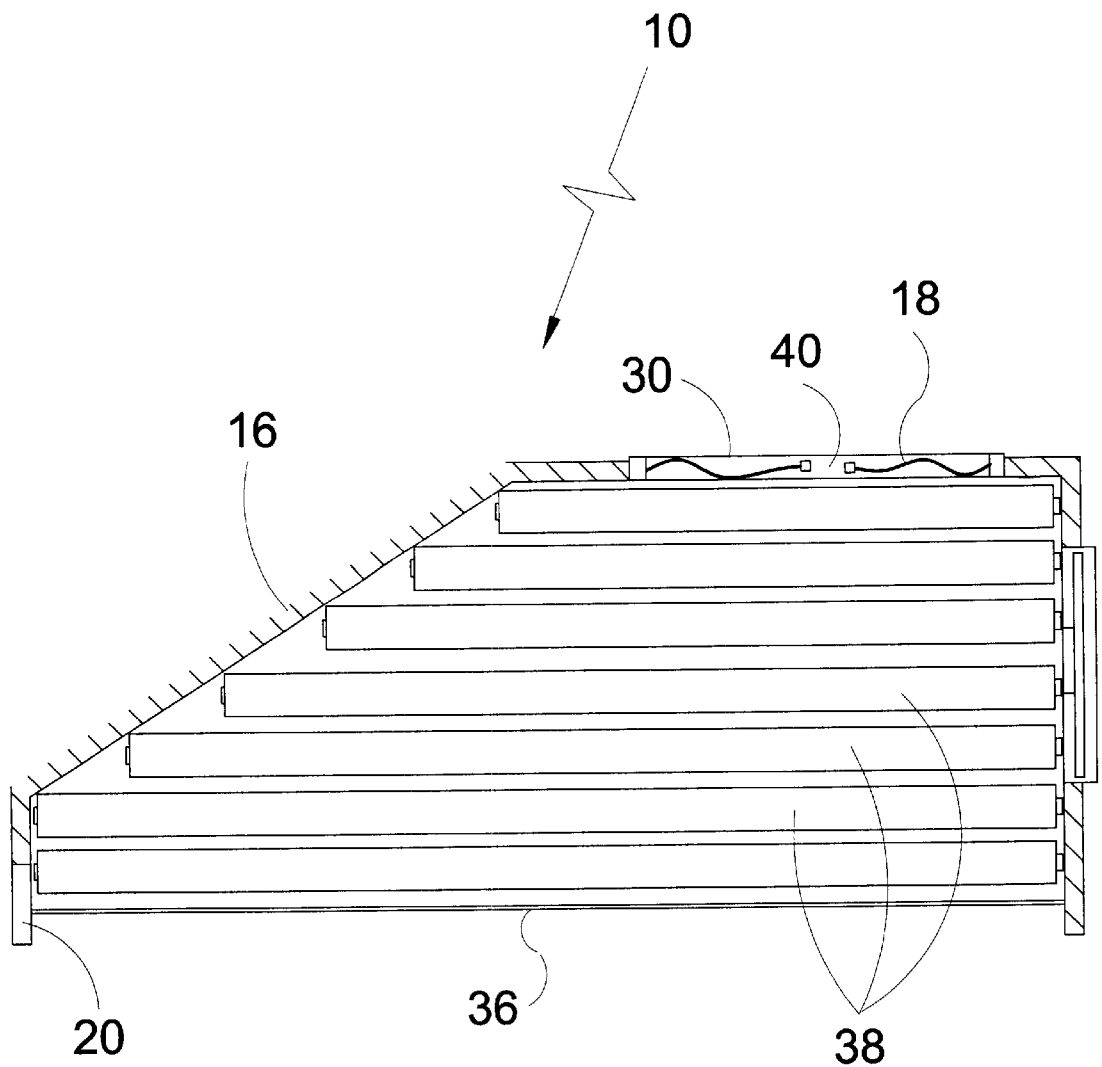
FIG. 7 is a side cutaway view of the present invention.

Turning to FIG. 7, shown therein is a side cutaway view of the present invention 10 showing a plurality of UV A and UV B generating bulbs 38 positioned on the interior of the device. Also shown is the screen foot support 36. Other elements previously disclosed are also shown.

Figure 8:
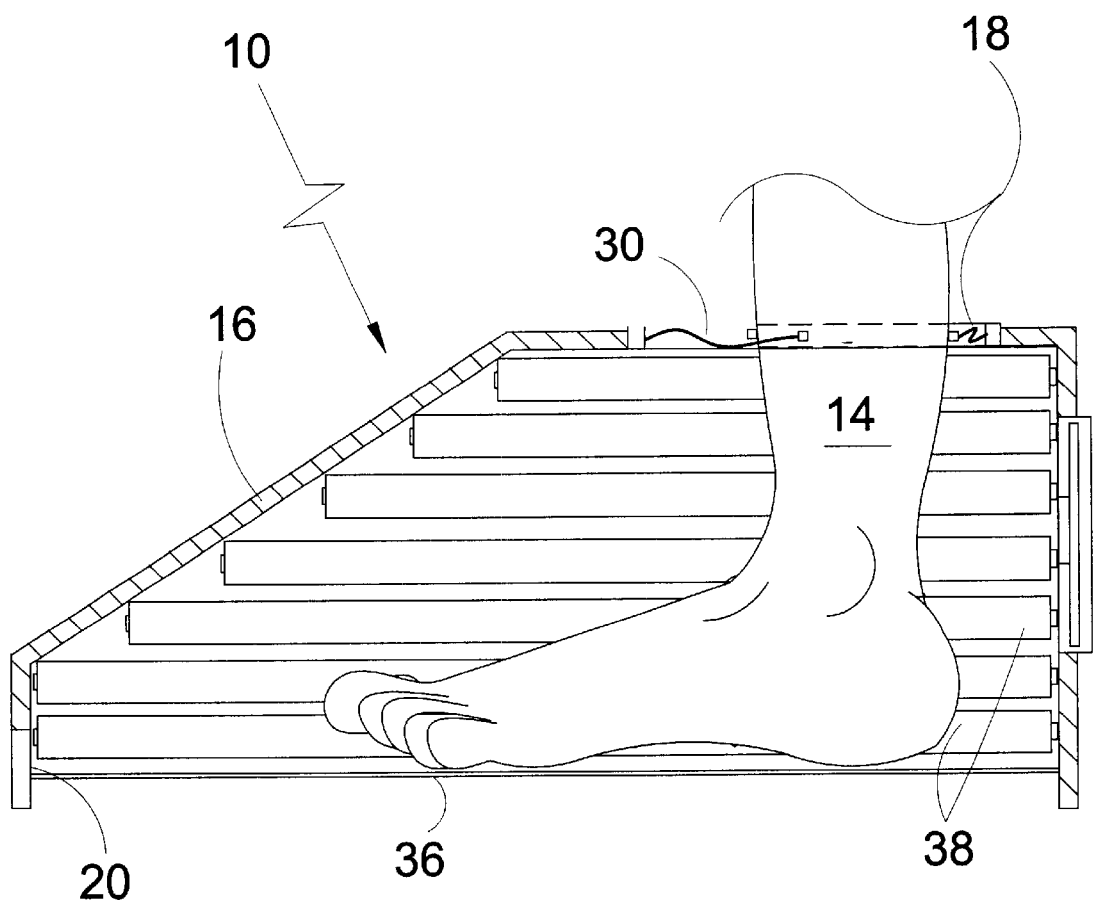
FIG. 8 is a cutaway view of the present invention.

Turning to FIG. 8, shown therein is a cutaway view of the present invention 10 showing a foot 14 resting on the screen platform 36 with a plurality of UV A and UV B generating bulbs 38 providing a tanning session for the enclosed limb. The sealing means 18 is also shown engaging the foot 14 of the user. Other elements previously disclosed are also shown.

Figure 9:
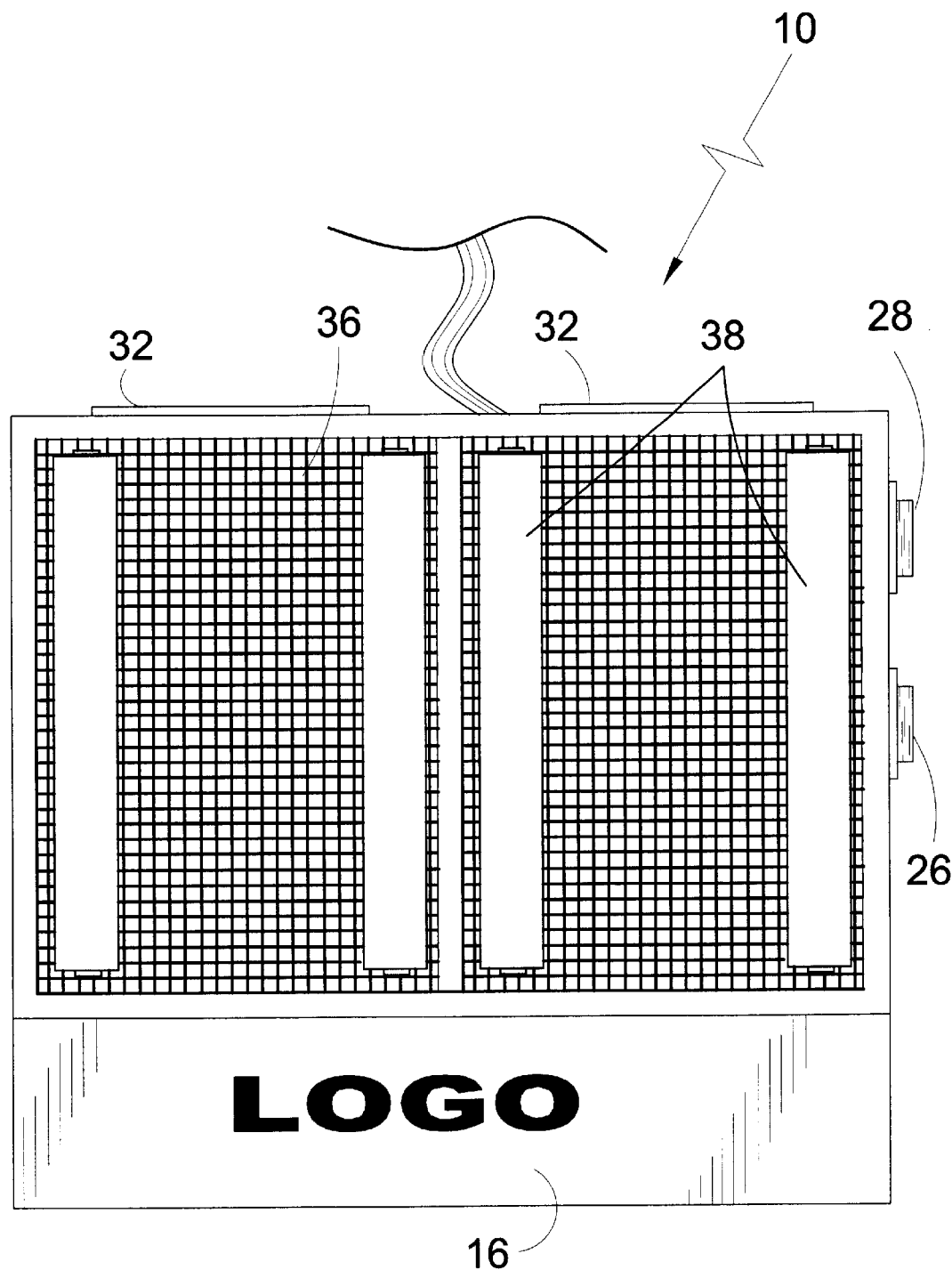
FIG. 9 is a cutaway view of the present invention.

Turning to FIG. 9, shown therein is a cutaway view of the present invention 10 showing a plurality of UV A and UV B light bulbs 38 positioned on the interior walls of the device. Also shown is the removable screen platform 36. Other elements previously disclosed are also shown.

Figure 10:
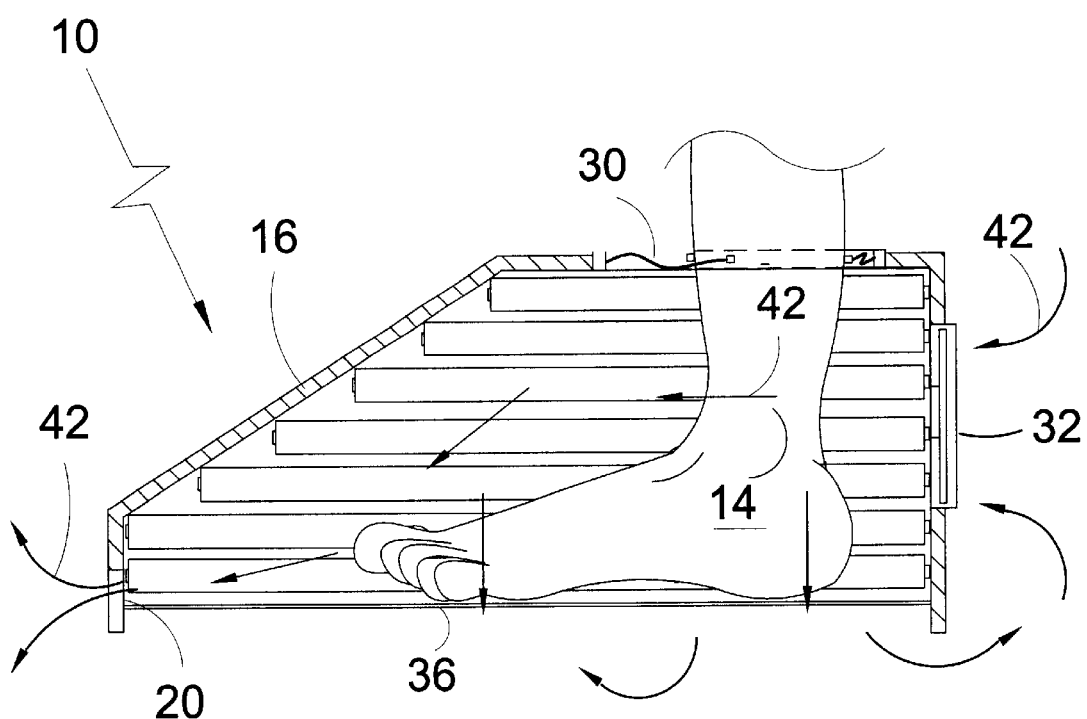
FIG. 10 is a interior view of the present invention.

Turning to FIG. 10, shown therein is a interior view of the present invention 10 showing air flow with arrows 42 within the tanning device. The fan 32 injects air into the device while the interior structure deflects the air currents around the limb 14 receiving the tanning session. The front air vents 20 and screen vents 36 allow the air to exit while fresh air is introduced by the fan 32. Other elements previously disclosed are also shown.

What is claimed to be new and desired to be protected by Letters Patent is set forth in the appended claims:

1. An apparatus for tanning feet and ankles, comprising:
   a) a housing, said housing having a top, a bottom, a rear, a pair of vertical side walls, and a front, said bottom comprising a screen member adapted to receive and support bottoms of said feet, said screen member being mounted within said housing so as to be above any floor on which said housing sits;
   b) said top of said housing having a pair of apertures therein for receiving the feet;
   c) means comprising an ultraviolet light source disposed internal to said housing whereby each foot and ankle are tanned, said light source comprising a plurality of extended bulbs in parallel relationship with each other horizontally disposed along each side wall of said housing and another plurality of extended bulbs in parallel relationship with each other horizontally disposed in a vertical column adapted to be between the feet and ankles of a user, said bulbs extending from the front to the rear of said housing;
   d) means for sealing around each ankle whereby ultraviolet light is retained internal said housing;
   e) means for ventilating said housing whereby the interior is cooled;
   f) means for controlling the apparatus whereby a user can control the apparatus; and,
   g) means for connection to a power source for the apparatus.

2. The apparatus of claim 1, wherein said means for sealing further comprises an elastomeric seal disposed internal said apertures on top of said housing.

3. The apparatus of claim 2, wherein said seal has a central aperture therein, said aperture of said seal for receiving the foot and ankle of a user.

4. The apparatus of claim 3, wherein said aperture of said seal has an inner surface thereon, said inner surface engaging the skin of the ankle of the user to retain ultraviolet light internal said housing.

5. The apparatus of claim 4, wherein said ultraviolet bulbs further comprise ultraviolet A light bulbs.

6. The apparatus of claim 5, wherein said ultraviolet bulbs further comprise ultraviolet B light bulbs.

7. The apparatus of claim 6, wherein said means for ventilating further comprises at least one electric fan disposed on said rear of said housing for forcing air into said housing.

8. The apparatus of claim 7, wherein said means for ventilating further comprises at least one air vent disposed on a wall of said housing for emitting air from said housing.

9. The apparatus of claim 8, having a vertical wall dividing said housing into two adjacent compartments for allowing each foot to be in adjacent compartments with separate rows of extended bulbs on opposite sides of said wall.

10. The apparatus of claim 9, wherein said means for controlling the apparatus further comprises an on/off switch.

11. The apparatus of claim 10, wherein said means for controlling the apparatus further comprises a timer switch for said ultraviolet lights.

12. The apparatus of claim 11, wherein said means for controlling the apparatus further comprises a timer switch for said fan.

13. The apparatus of claim 12 wherein said front of said housing has a forward sloping flat surface for display of a logo thereon.

* * * * *